US009823192B1

United States Patent
Chan et al.

(10) Patent No.: US 9,823,192 B1
(45) Date of Patent: Nov. 21, 2017

(54) AUTO-CALIBRATION SURFACE PLASMON RESONANCE BIOSENSOR

(71) Applicants: Benny L. Chan, Fremont, CA (US); Suganda Jutamulia, Berkeley, CA (US)

(72) Inventors: Benny L. Chan, Fremont, CA (US); Suganda Jutamulia, Berkeley, CA (US)

(73) Assignee: Ecolife Technologies, LLC, Fremont, CA (US)

( * ) Notice: Subject to any disclaimer, the term of this patent is extended or adjusted under 35 U.S.C. 154(b) by 0 days.

(21) Appl. No.: 15/330,601

(22) Filed: Oct. 17, 2016

(51) Int. Cl.
*G01N 21/55* (2014.01)
*G01N 21/552* (2014.01)
*G02B 5/04* (2006.01)
*G01J 1/02* (2006.01)

(52) U.S. Cl.
CPC ........ *G01N 21/553* (2013.01); *G01J 1/0266* (2013.01); *G02B 5/04* (2013.01); *G01N 2201/127* (2013.01)

(58) Field of Classification Search
CPC .. G01N 21/552; G01N 21/553; G01N 21/554; G01N 21/274; G01N 21/55
USPC ........................................................ 356/445
See application file for complete search history.

(56) References Cited

U.S. PATENT DOCUMENTS

| | | | |
|---|---|---|---|
| 6,420,984 B1 | 7/2002 | Robertson | |
| 6,594,018 B1 | 7/2003 | Bartholomew | |
| 7,197,196 B2 | 3/2007 | Lin et al. | |
| 7,465,588 B2 | 12/2008 | Muraishi et al. | |
| 7,751,052 B2* | 7/2010 | Pyo | G01N 21/553 356/445 |
| 2005/0087442 A1 | 4/2005 | Elkind | |
| 2006/0274434 A1 | 12/2006 | Mino et al. | |
| 2011/0128548 A1 | 6/2011 | Chinowsky et al. | |
| 2011/0215705 A1 | 9/2011 | Long et al. | |
| 2011/0310394 A1 | 12/2011 | Li | |
| 2013/0214138 A1* | 8/2013 | Chiarello | G01N 21/431 250/227.11 |
| 2015/0300954 A1* | 10/2015 | Chan | G01N 21/553 422/82.05 |

* cited by examiner

*Primary Examiner* — Hoa Pham
(74) *Attorney, Agent, or Firm* — Suganda Jutamulia (57) ABSTRACT

A surface plasmon resonance biosensor comprises: a prism, an incident light incident to a side of the prism and reflected at the side of the prism, the incident light comprising a first incident light having a first incident angle and a second incident light having a second incident angle, and a detector comprising pixels for detecting the incident light reflected at the side of the prism, where positions of pixels of the detector correspond to incident angles of the incident light, and where positions of pixels of the detector are calibrated by at least the first incident light having the first incident angle and the second incident light having the second incident angle.

20 Claims, 10 Drawing Sheets

AUTO-CALIBRATION SURFACE PLASMON RESONANCE BIOSENSOR

FIELD OF THE INVENTION

This invention relates to a surface plasmon resonance biosensor that is capable of measuring the refractive index of a fluid.

BACKGROUND OF THE INVENTION

Surface plasmon resonance (SPR) affinity biosensor relies on the measurement of the molecular binding induced refractive index changes and therefore it is label-free technology. Due to its high sensitivity, selectivity, and real-time measurement capability, SPR biosensor has become the technology of choice for researchers within the pharmaceutical and biomedical industry to characterize molecular interaction kinetic, thermodynamics, and concentration. SPR biosensors can support an incredible range of applications from qualitative binding to high resolution kinetic analysis. Nearly any interaction involving biological systems including low molecular weight components, proteins, nucleic acids, antibody, and even lipid surface environments are amenable to these instruments.

SPR biosensors are based on the measurement of refractive index of the fluid under test. The refractive index is indicated by a dark bar in a light band detected by a detector such as CMOS image sensor. The position of the dark bar indicates the SPR resonance angle, which in turn, indicates the refractive index of the fluid under test. To perform reliable measurement, the relation between the position of the dark bar and the SPR resonance angle must be calibrated. The ideal situation is the calibration is provided for each measurement, such that an auto-calibration SPR biosensor can be realized.

The SPR based technology continues to expand and improve to become an indispensable analytical tool in biomedical research. Although a tremendous progress has been made in modern days SPR equipment, simple and precise detection method is still in demand. Accordingly, auto-calibration SPR biosensor is still in demand.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

Corresponding reference characters indicate corresponding components throughout the several views of the drawings. Skilled artisans will appreciate that elements in the figures are illustrated for simplicity and clarity and have not necessarily been drawn to scale. For example, the dimensions of some of the elements in the figures may be exaggerated relative to other elements to help to improve understanding of various embodiments of the present invention.

DETAILED DESCRIPTION

In the following description, numerous specific details are set forth in order to provide a thorough understanding of the present invention. It will be apparent, however, to one having ordinary skill in the art that the specific detail need not be employed to practice the present invention. In other instances, well-known materials or methods have not been described in detail in order to avoid obscuring the present invention.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment. Furthermore, the particular features, structures or characteristics may be combined in any suitable combinations and/or sub-combinations in one or more embodiments.

Figure 1:
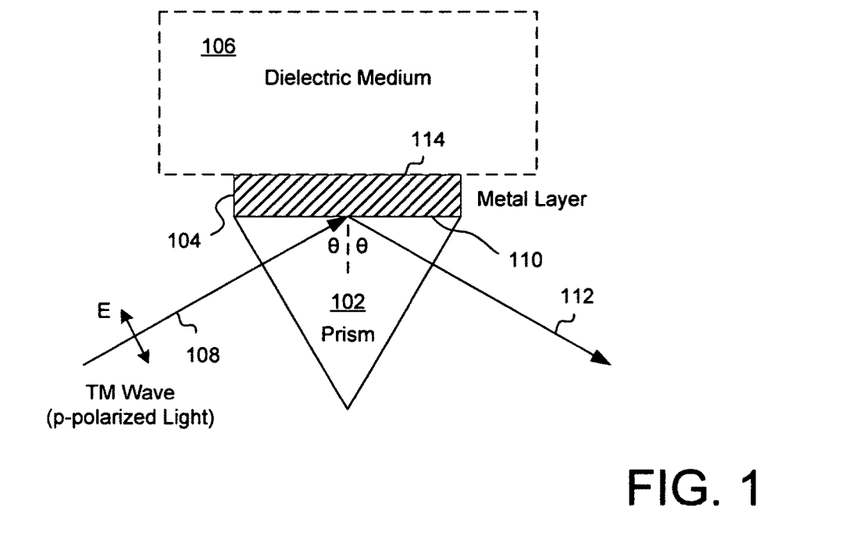
FIG. 1 shows an embodiment of the Kretschmann configuration using prism coupling to generate SPR.

FIG. 1 shows an embodiment 100 of the Kretschmann configuration using prism coupling to generate SPR. Embodiment 100 of the Kretschmann configuration typically comprises a glass prism 102. A side of glass prism 102 is coated with a thin metal layer 104. For example, thin metal layer 104 may have a thickness of about 50 nm. Thin metal layer 104 is in direct contact with a dielectric medium 106 of lower refractive index. The dielectric medium may be a fluid. When a TM wave (p-polarized) light 108, is incident through prism 102 on a prism metal interface 110, the incident light 108 is reflected to be a reflected light 112. When an incident angle θ of incident light 108 is larger than the critical angle between prism 102 and dielectric medium 106 without thin metal layer 104, an evanescent wave is produced perpendicular to prism metal interface 110. The evanescent wave propagates from prism 102 into dielectric medium 106 through thin metal layer 104 and decays exponentially. The evanescent wave is characterized by incidence angle θ of incident light 108 and the dielectric constant of prism 102.

The surface plasmon wave (SPW) is a TM electromagnetic wave which propagates at an interface 114 between dielectric medium 106 and thin metal layer 104. The SPW is characterized by the dielectric constants of thin metal layer 104 and the dielectric constant of dielectric medium 106. At a particular resonance incidence angle, θ-resonance, of incident light 108, the energy of the evanescent wave is transferred to excite the SPW. Accordingly, the intensity of reflected light 112 is reduced when the energy of incident beam 108 is transferred to the SPW through the evanescent wave. Note that the reflected angle is the same as the incident angle.

Figure 2:
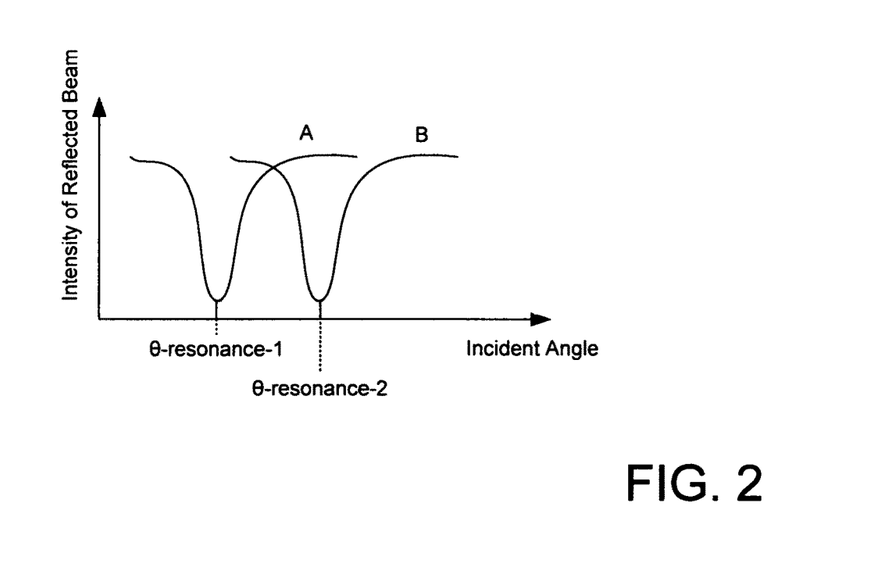
FIG. 2 shows the intensity of the reflected beam as function of incident angle θ.

FIG. 2 shows the intensity of reflected light 112 as function of incident angle θ. At the resonance condition, there is transfer of energy from incident light 108 to SPW propagating at interface 114 resulting in a reduction of intensity of reflected light 112. The intensity of reflected light 112 of curve A shows a sharp dip at resonance angle θ-resonance-1. The value of 0-resonance-1 can be determined from curve A, which may be obtained from measurement. If the dielectric constants of prism 102 and thin metal layer 104 are known, the dielectric constant of dielectric medium 106 can be determined. Thus the dielectric constant and also the refractive index of dielectric medium 106 in contact with thin metal layer 104 can be determined. Furthermore, when the refractive index of dielectric medium 106 changes, the reflectance dip shifts to another angle accordingly. For example curve A shifts to curve B, 0-resonance-1 shifts to 0-resonance-2. If the refractive index of a fluid is related to the concentration of a component in the fluid, the concentration of the component can be determined as well.

Figure 3:
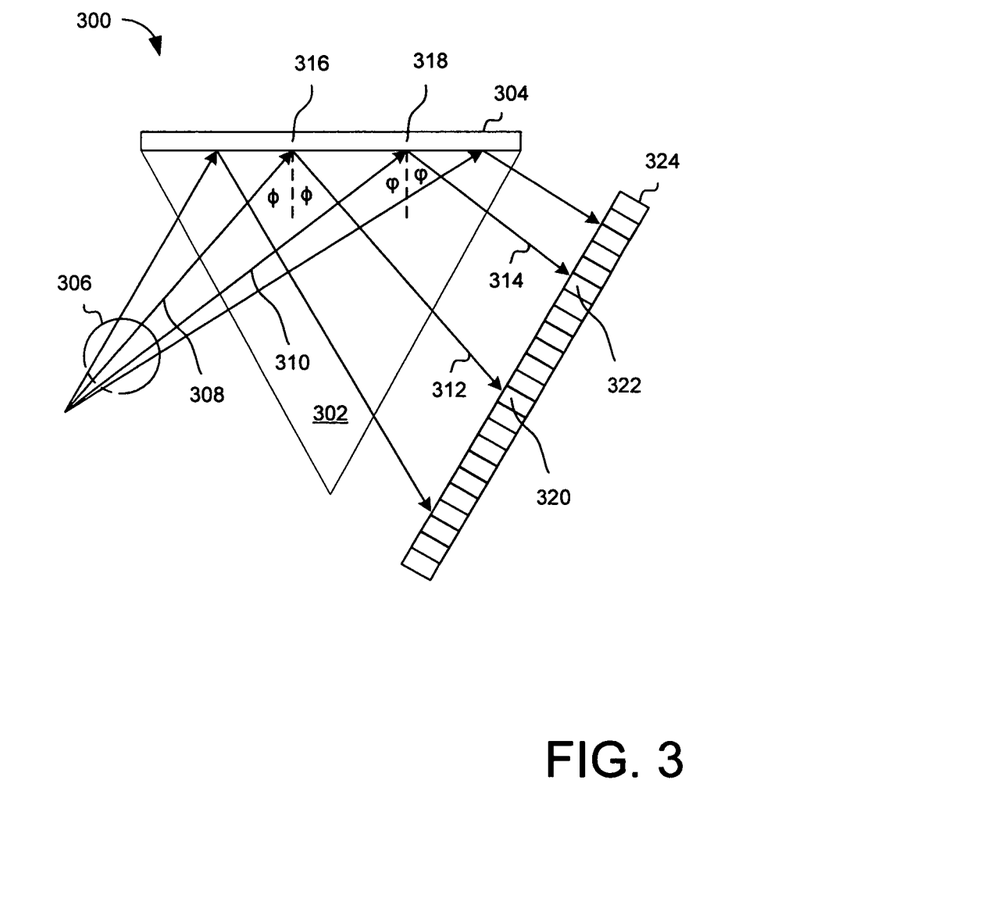
FIG. 3 shows an optical assembly of SPR biosensor according to the present invention.

FIG. 3 shows an optical assembly 300 of SPR biosensor according to the present invention. In assembly 300, an incident light 306 comprises an incident light 308 having an incident angle φ at the interface of an prism 302 and a thin metal layer 304, and an incident light 310 having an incident angle φ at the interface of prism 302 and thin metal layer 304. Incident light 308 is reflected at a position 316 of the interface of prism 302 and thin metal layer 304 becoming a reflected light 312. Incident light 310 is reflected at a position 318 of the interface of prism 302 and thin metal layer 304 becoming a reflected light 314. Reflected light 312 leaving prism 302 arrives at a pixel position 320 of a detector 324. Reflected light 314 leaving prism 302 arrives at a pixel position 322 of detector 324. Note that the reflected angle is the same as the incident angle.

Incident light 306 may be a fan-shape light sheet as described in U.S. patent application Ser. No. 14/120,049, of the same inventors, which is incorporated herein by reference in its entirety. In an embodiment, incident light 306 may have a prism shape rather than a fan shape, as described below.

Figure 4A:
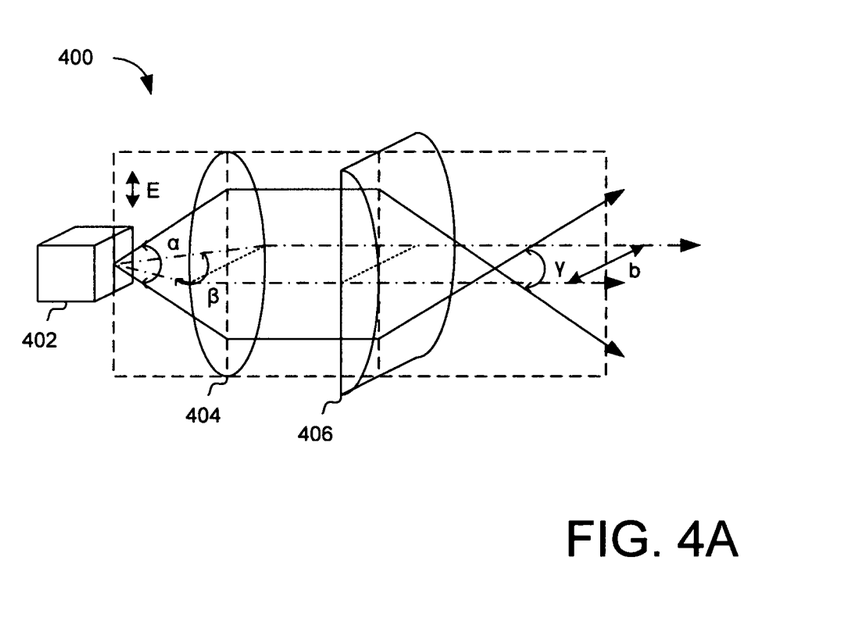
FIG. 4A shows a laser line generator according to the present invention.

FIG. 4A shows a laser line generator 400 according to the present invention. Laser line generator comprises a laser diode (semiconductor laser) 402 that emits a TM wave (p-polarized) laser light having short-axis divergent angle α and long-axis divergent angle β. The emitted laser light is collimated by a collimating lens 404. The collimated light passes a cylindrical lens 406 that spreads the light along the short axis with a divergent angle γ, while keeps the light collimated along the long axis with a thickness of b. If b is small compared with the spreading of angle γ (e.g., A2 in FIG. 6C), a fan-shape light sheet with divergent angle γ and thickness b may be formed. If b is large compared with the spreading of angle γ (e.g., A2 in FIG. 6C), a prism-shape light with prism angle (divergent angle) γ and prism length b (thickness b) may be formed. A fan-shape light sheet may be considered as a slice of the cross-section of a prism-shape light. Other laser line generators are possible as shown in FIGS. 4B and 4C.

Figure 4B:
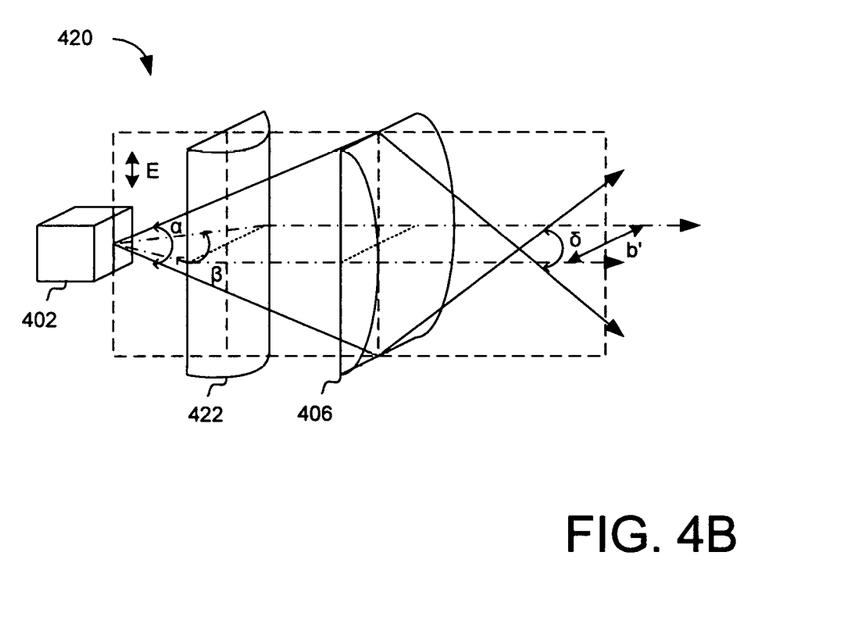
FIG. 4B shows a laser line generator according to the present invention.

FIG. 4B shows a laser line generator 420 according to the present invention. Laser line generator 420 uses a cylindrical lens 422 replacing collimating lens 404 of FIG. 4A. Cylindrical lens 422 collimates the emitted laser beam along the long axis with a thickness b'. Cylindrical lens 422 does not change the short-axis divergent angle α. Cylindrical lens 406 changes the short-axis divergent a to a divergent angle δ. Cylindrical lens 406 does not change the beam along the long axis. A fan-shape light sheet or prism-shape light with divergent angle δ and thickness b' may be formed.

Figure 4C:
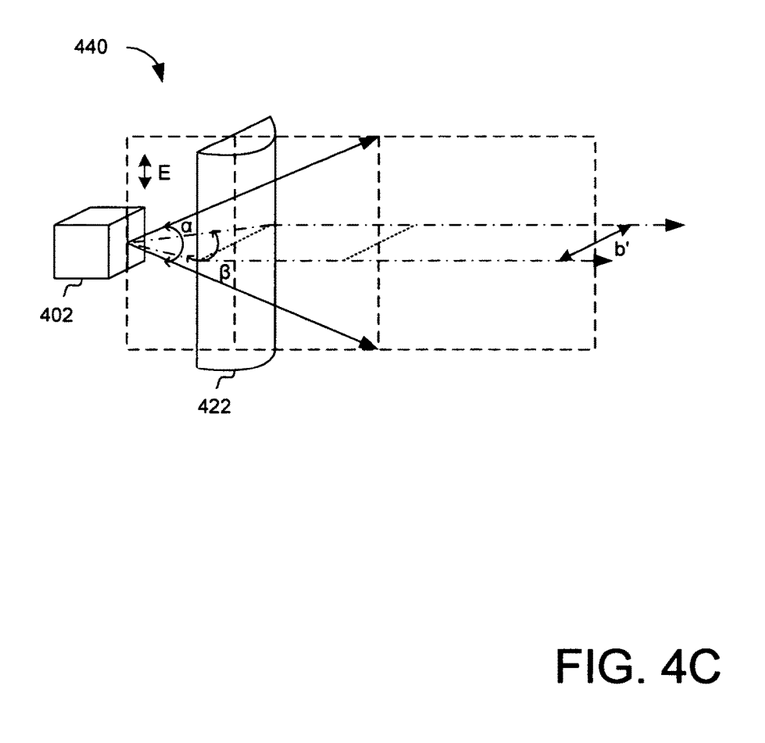
FIG. 4C shows a laser line generator according to the present invention.

FIG. 4C shows a laser line generator 440 according to the present invention. Laser line generator 440 uses cylindrical lens 422 only without collimating lens 404 and cylindrical lens 406 of FIG. 4A. A fan-shape light sheet or prism-shape light with divergent angle α, which is the short-axis divergent angle of the emitted laser beam, and thickness b' may be formed.

Figure 5A:
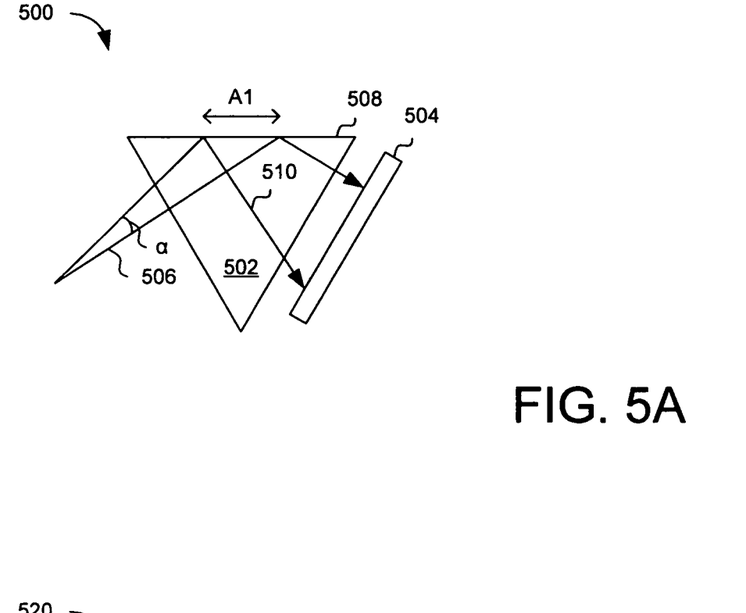
FIG. 5A shows an optical assembly comprising a prism and a detector according to the present invention.

FIG. 5A shows an optical assembly 500 comprising a prism 502 and a detector 504, according to the present invention. Detector 504 may be a 1D linear detector or a 2D array detector (2D image sensor). A fan-shape laser light sheet or a prism-shape light 506 having a divergent angle α is incident on a side surface 508 of prism 502. A light spot (e.g., square) having a width A1 is formed on side surface 508 of prism 502. A thin metal layer is coated on side surface 508. A fluid dielectric medium is disposed on the thin metal layer. The fluid dielectric medium may be a liquid solution or gas. A SPW is generated by incident light 506 having a particular resonance incident angle. At the resonance incident angle, the intensity of a reflected light 510 decreases.

Detector 504 detects the reduction of intensity of reflected light 510 at the resonance incident angle. Detector 504 detects the intensity of reflected light 510 at all incident angles within a range. Each element or pixel of detector 504 may correspond to an incident angle within the range. Note that the reflected angle is the same as the incident angle.

Figure 5B:
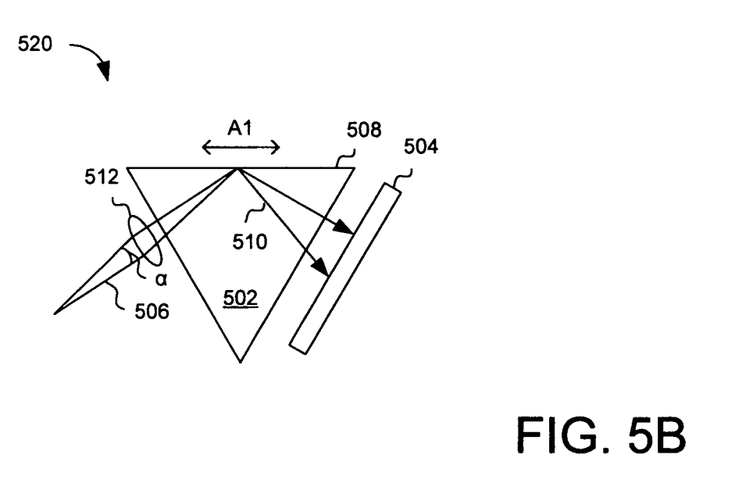
FIG. 5B shows an optical assembly comprising a prism and a detector according to the present invention.
Figure 5C:
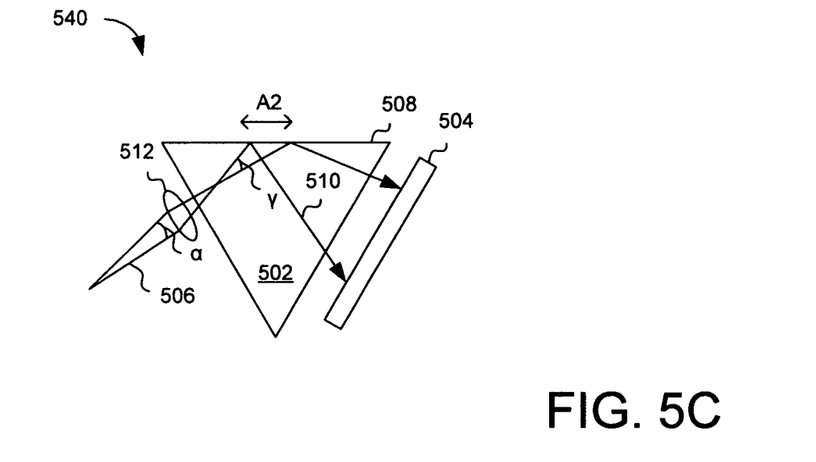
FIG. 5C shows an optical assembly comprising a prism and a detector according to the present invention.

FIG. 5B shows an optical assembly 520 similar to optical assembly 500 of FIG. 5A, according to the present invention. The difference between optical assembly 520 and optical assembly 500 is that incident light 506 is focused by a focusing lens 512 on side surface 508. Focusing lens may be a cylindrical lens. FIG. 5C shows another optical assembly 540 similar to optical assembly 500 of FIG. 5A, according to the present invention. The difference between optical assembly 540 and optical assembly 500 is that incident light 506 is focused by focusing lens 512 at the proximity of side surface 508 before or after (not shown) it reaches side surface 508. A fan-shape laser light sheet or prism-shape light having a divergent angle γ is incident on side surface 508 of prism 502. A light spot (e.g., square) having a width A2 is formed on side surface 508 of prism 502.

Figure 5D:
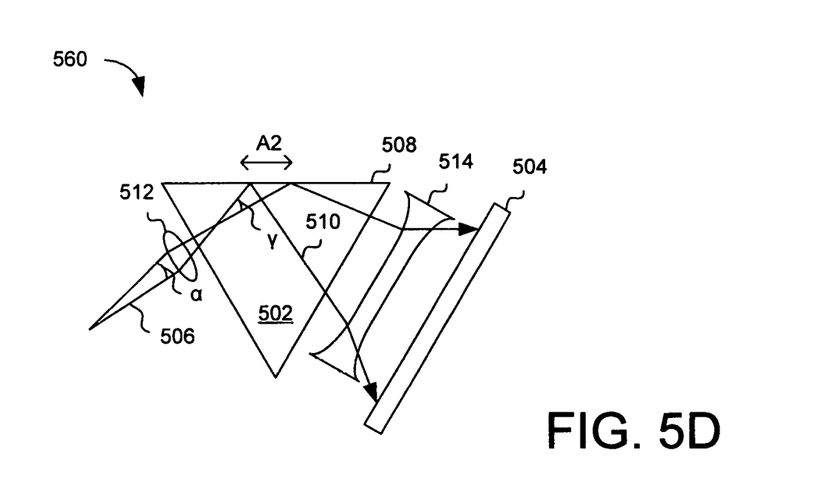
FIG. 5D shows optical assembly of FIG. 5C further comprising a diverging lens according to the present invention

FIG. 5D shows an optical assembly 560 similar to optical assembly 540 of FIG. 5C, according to the present invention. The difference between optical assembly 560 and optical assembly 540 is that it includes a diverging lens 514 to increase diverging angle γ of reflected light 510. Diverging lens 514 may be a cylindrical lens. In this manner, detector 504 may detect signals having better angular resolution. It is appreciated that optical assembly 500 of FIG. 5A and optical assembly 520 of FIG. 5B may include a diverging lens as well.

Figure 6A:
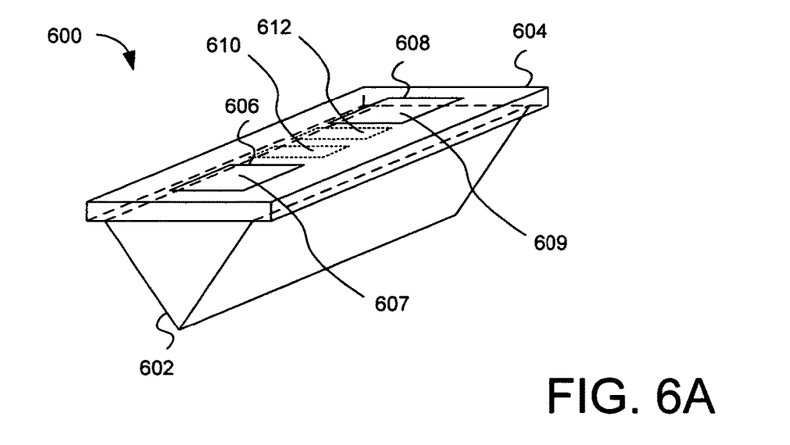
FIG. 6A shows an exemplary prism of SPR biosensor according to the present invention.

FIG. 6A shows an exemplary prism assembly 600 of SPR biosensor according to the present invention. Prism assembly 600 comprises a prism 602 and a tray 604 mounted on prism 602. Tray 604 and prism 602 form at least one cell 607 for providing a fluid dielectric medium for measurement. Prism assembly 600 also comprises a thin metal layer (not shown in FIG. 6A) coated on the surface of the prism in cell 607 between the fluid dielectric medium and prism 602. Tray 604 may have at least one through window 606 for forming at least one cell 607. Tray 604 may be a silicon tray. Tray 604 may be a molded plastic tray or a metal tray as well.

For example, tray 604 comprises a first through window 606 for forming a first cell 607 on prism 602, a second through window 608 for forming a second cell 609 on prism 602, a first half-through cavity 610 facing prism 602, and a second half-through cavity 612 facing prism 602. Epoxy, glue, cement, or other adhesives may be used for mounting tray 604 on prism 602.

It is appreciated that tray 604 may comprise only one through window forming only one cell or more than two through windows forming more than two cells as well. For example, only one through window forms one cell. In an embodiment, tray 604 may comprise more than two through windows and prism assembly 600 has more than two cells that may be used for multiple detections. In another embodiment, tray 604 may comprise only one through window forming only one cell. The surface of prism 602 in the cell or cells is coated with a thin metal layer (not shown in FIG. 6A). For example, the metal may be gold, silver, aluminum, copper, or any suitable metal.

Figure 6B:
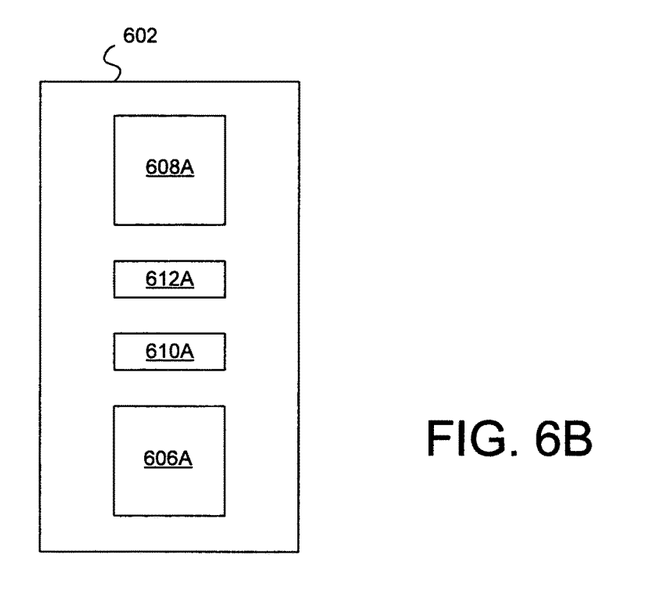
FIG. 6B shows schematically top view of the prism of FIG. 6A according to the present invention.

FIG. 6B shows schematically a top view of exemplary prism 602 according to the present invention. As seen in FIG. 6A, tray 604 comprises first through window 606, second through window 608, a first half-through cavity 610 facing prism 602, and a second half-through cavity 612 facing prism 602. FIG. 6B shows an area 606A on the top of prism 602 under first through window 606, an area 608A on the top of prism 602 under second through window 608, an area 610A on the top of prism 602 under first half-through cavity 610, and an area 612A on the top of prism 602 under first half-through cavity 610. Area 610A is separated from area 612A. All areas 606A, 608A, 610A, and 612A are separated from each other. Tray 604 is disposed on the top of prism 602. Area 606A and area 608A are coated with a thin metal layer.

A fluid dielectric medium for measurement is disposed on area 606A provided through first through window 606. A different or same fluid dielectric medium for measurement is disposed on area 608A provided through second through window 608. Only air is on area 610A and area 612A, since they are under first half-through cavity 610 and second half-through cavity 612 facing prism 602, respectively. Alternatively, area 610A and/or area 612A may be under the same or different fluid dielectric medium provided before they are covered by first half-through cavity 610 and second half-through cavity 612 facing prism 602, respectively.

Area 610A and area 612A are for providing reference signals of reflected light 312 having reflected angle $\phi$ and reflected light 314 having reflected angle $\phi$, respectively, as shown in FIG. 3. In an embodiment, reflected angle $\phi$ is the critical angle of prism 602. In this configuration, area 610A is not coated with the thin metal layer, and only air on area 610A. In an embodiment, reflected angle $\phi$ is the SPR resonance angle of prism 602 and gold and air. Area 612A is coated with a thin gold layer, and only air on area 612A. In an embodiment, reflected angle$_9$ is the SPR resonance angle of prism 602 and silver and air. Area 612A is coated with a thin silver layer, and only air on area 612A. It is appreciated that other combinations are possible. Other combinations may comprise other metal layers and/or fluid dielectric media other than air.

Figure 7:
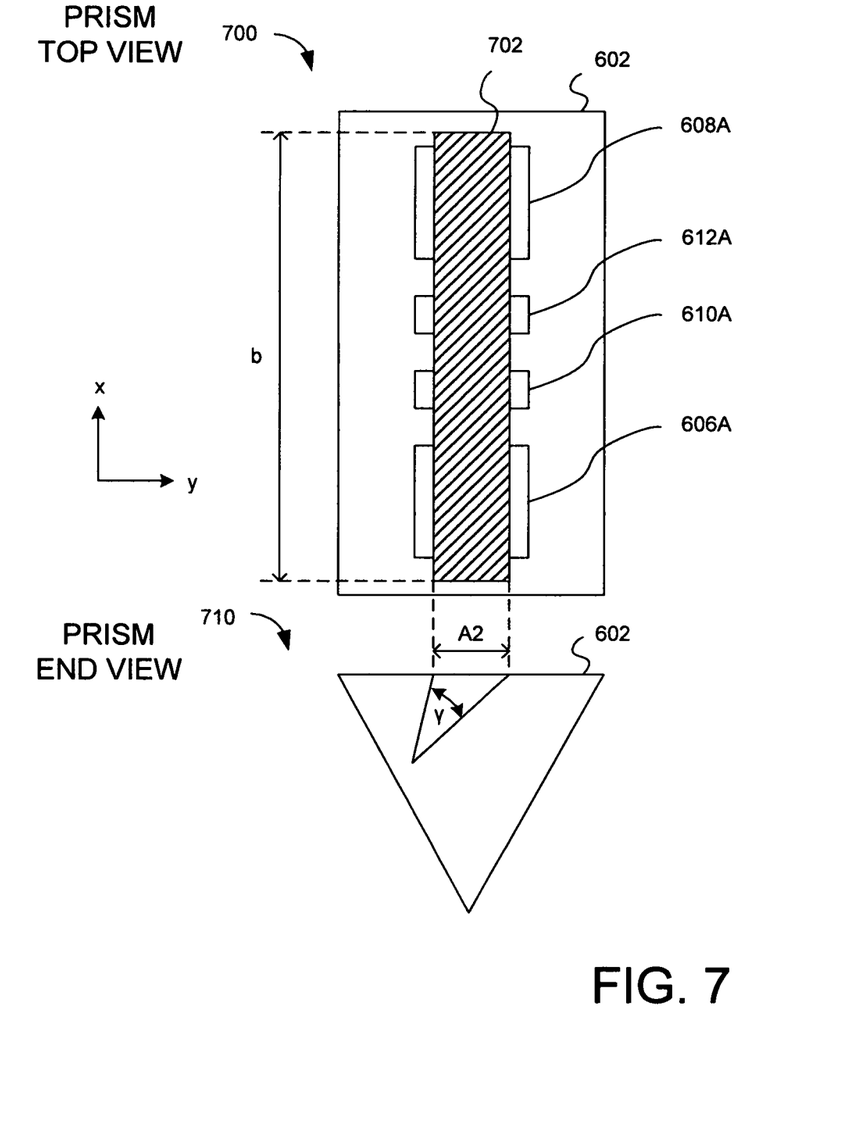
FIG. 7 shows top view and end view of the prism of FIG. 6A according to the present invention.

FIG. 7 shows a prism top view 700 and a prism end view 710. For example, top surface of prism 602 has areas 606A, 608A, 610A, and 612A. A fluid dielectric medium is disposed on area 606A. A different or same fluid dielectric medium is disposed on area 608A. Top surface of prism 602 may have only one area (e.g., 606A) having fluid dielectric medium, and may have more than two areas (e.g., 606A and 608A) having fluid dielectric media. Areas 610A and 612A are for generating reference signals to calibrate the relation between the pixel position and the reflected angle (e.g., reflected angle $\theta$ of FIG. 1) at the interface of the prism and the thin metal layer. It is appreciated than more than two areas for generating reference signals are possible.

An incident light 702 sufficiently covers all areas 606A, 608A, 610A, and 612A of top surface of prism 602. Incident light 702 may be prism-shape light generated by a laser line generator such as laser line generators 400, 420, and 440 in FIGS. 4A, 4B, and 4C, respectively. Prism length b (thickness b) of the prism-shape incident light 702 covers all areas 606A, 608A, 610A, and 612A along the x-direction. The spreading A2 of divergent angle $\gamma$ is perpendicular to thickness b, along the cross-section of prism 602 parallel to the end of prism 602. The spreading A2 of divergent angle $\gamma$ is along the y-direction. In this manner, all areas 606A, 608A, 610A, and 612A are covered by incident light having all incident angles and reflected angles use in the measurement, including reflected angles $\theta$ and $\phi$ of FIG. 3.

If incident light 702 is a focused light as shown in FIG. 5B, spreading A2 in FIG. 7 will be the width of the focused light. In this situation, incident light 702 in FIG. 7 becomes a thin line having a width being the width of the focused light.

For example, area 610A generates reflected light having reflected angle $\phi$ as a first reference signal, and area 612A generates reflected light having reflected angle $\phi$ as a second reference signal, as shown in FIG. 3. Referring to FIG. 2, the light reflected from area 610A comprises a sharp dip at reflected angle $\phi$. In other words, the reflected light at reflected angle $\phi$ has reduced intensity as compared with reflected light at other reflected angle. Similarly, the light reflected from area 612A comprises a sharp dip at reflected angle $\phi$. In other words, the reflected light at reflected angle $\phi$ has reduced intensity as compared with reflected light at other reflected angle.

In this manner, since the positions of the pixels correspond to reflected angle of light, by looking at the reflected light from area 610A, pixel position 320 of detector 324 may be calibrated that it is associated with reflected angles $\phi$, as shown in FIG. 3. By looking at the reflected light from area 612A, pixel position 322 of detector 324 may be calibrated that it is associated with reflected angles $\phi$, as shown in FIG. 3.

Referring to FIG. 3, if only one pixel position is calibrated, for example, pixel position 320 corresponds to reflected angle $\phi$, one may not define reflected angles that correspond to other pixel positions. However, if two pixel positions are calibrated, for example, pixel position 320 corresponds to reflected angle $\phi$ and pixel position 322 corresponds to reflected angle $\phi$, one may define reflected angles that correspond to other pixel positions based on an interpolation and extrapolation of two pixel positions 320 and 322. Accordingly, all pixel positions of detector 324 may be calibrated to associate with reflected angles. It is appreciated that reflected angle is the same as the incident angle.

Thus, an auto-calibration SPR biosensor can be constructed. It is appreciated that the relation between the pixel positions of the detector and the reflected angles is also analytically derived. For example, the relation may be obtained from ZEMAX or other ray tracing software that includes law of reflection and refraction, e.g., Snell's law. The calibration using one or two reflected angles may make the measurement more accurate. Of course, more than two reflected angles may be used. It is appreciated that reflected angle is the same as the incident angle.

The auto-calibration is an important feature for SPR biosensors, especially for a SPR biosensor using disposable prisms as disclosed in U.S. patent application Ser. No. 14/120,049, of the same inventors, which is incorporated herein by reference in its entirety. Since the prism is disposable, a new prism is installed in the optical assembly for each measurement. A misalignment thus can be corrected by the auto-calibration. The data reading becomes more precise and reliable. Prism 602 may be the disposable prism described in U.S. patent application Ser. No. 14/120,049.

Referring to FIG. 6A, the function of half-through cavities 610 and 612 facing prism 602 is to provide calibration reference signal. In an embodiment, half-through cavity 610 may contain air. No metal layer is coated on the surface of prism 602 in half-through cavity 610. The critical angle is defined at the interface of prism and air. For example, the prism may be made of glass having an index of refraction of 1.5. The index of refraction of air is 1. Thus, the critical angle is 41.81° (sin 41.81°=1/1.5). If the incident angle at the interface is equal or larger than 41.81° it will be reflected, and if the incident angle is less than 41.81°, the incident light will leave the prism and will not be reflected. Accordingly, the boundary of the detected reflected light and undetected transmitted light at the detector corresponds to the critical angle, which may be used for calibration of the incident angle of reflected light at the detector.

The calibration reference signal may be provided by SPR resonance angle as well. In an embodiment, the surface of prism 602 in second half-through cavity 612 is coated with the same thin metal layer as through windows 606 and 608. The detected dark bar will correspond to the SPR resonance angle, which may be used for calibration of the incident angle of reflected light at the detector. The detected dark bar corresponds to the sharp dip of curve A or B in FIG. 2.

Figure 8:
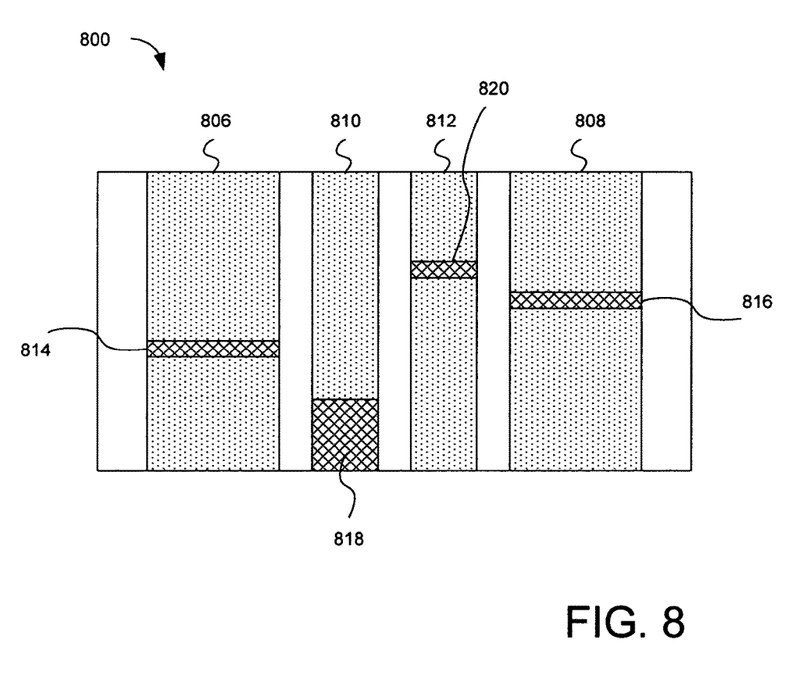
FIG. 8 shows schematically an exemplary light pattern projected on a 2D image sensor according to the present invention.

FIG. 8 shows an exemplary light pattern 800 projected on a CMOS 2D image sensor, which may be detector 504 in optical assemblies 500, 520, 540, and 560 of FIGS. 5A-5D, according to the present invention. For example, there are four bands of light 806, 810, 812, and 808. Band 806 may correspond to the first through window 606, band 808 may correspond to the second through window 608, band 810 may correspond to first half-through cavity 610, and band 812 may correspond to second half-through cavity 612. Bands 810 and 812 are for calibration. The critical angle signal generated in first half-through cavity 606 is indicated by the boundary of bright part 810 and a dark part 818. A dark bar 820 in band 812 indicates the reference SPR resonance angle signal generated in second half-through cavity 612. The resonant angle signal generated in first through window 606 is indicated by a dark bar 814 in band 806, and the resonant angle signal generated in second through window 608 is indicated by a dark bar 816 in band 808. The dark bar corresponds to the sharp dip of curve A or B in FIG. 2.

The critical angle of light band 810 and the resonance angle of dark bar 820 can be interpolated and/or extrapolated to determine the resonance angles of dark bars 814 and 816. The positions of dark bars and critical angle signal are for illustration only. The actual positions and order of dark bars and critical angle signal may be different from light pattern 800 shown in FIG. 8.

In an embodiment, the surface of prism 602 in first half-through cavity 610 is coated with the same thin metal layer (e.g., gold) as through windows 606 and 608. The surface of prism 602 in second half-through cavity 612 is coated with different thin metal layer (e.g., silver) from through windows 606 and 608. Half-through cavities 610 and 612 contain air. The detected dark bars will correspond to the SPR resonance angles generated in first half-through cavity 610 and second half-through cavity 612, which may be used for calibration of the incident angle of reflected light at the detector.

Figure 9:
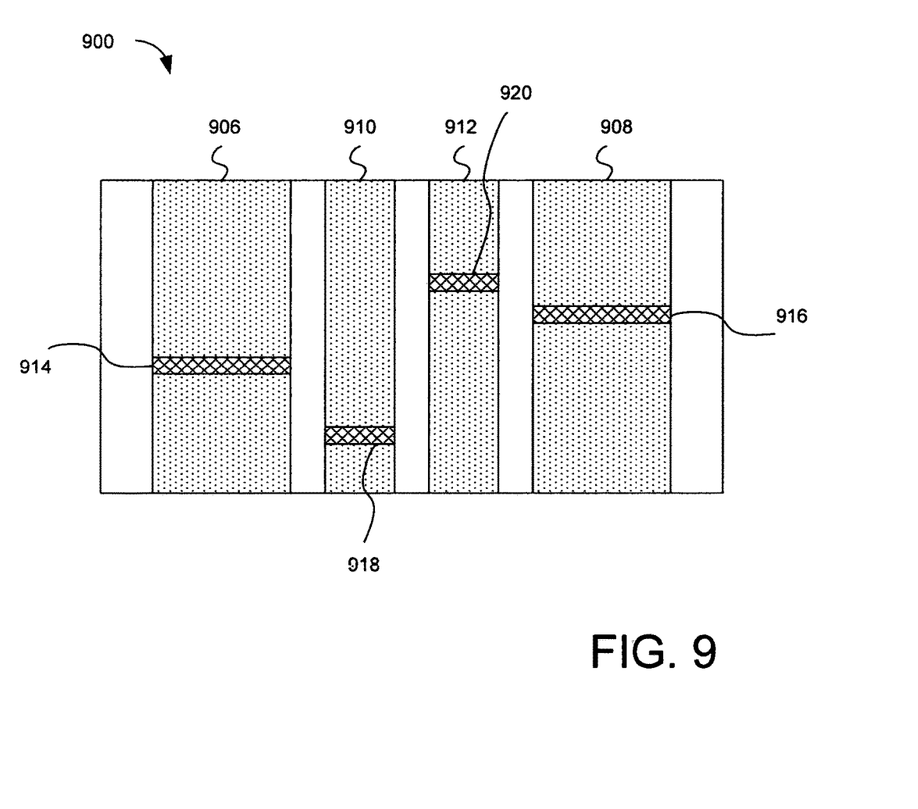
FIG. 9 shows schematically an exemplary light pattern projected on a 2D image sensor according to the present invention.

FIG. 9 shows an exemplary light pattern 900 projected on the CMOS 2D image sensor, similar to FIG. 8, according to the present invention. For example, there are four bands of light 906, 910, 912, and 908. Band 906 may correspond to the first through window 606, band 908 may correspond to the second through window 608, band 910 may correspond to first half-through cavity 610, and band 912 may correspond to second half-through cavity 612. Bands 910 and 912 are for calibration. A dark bar 918 in band 910 indicates the reference SPR resonance angle signal generated in first half-through cavity 610. A dark bar 920 in band 912 indicates the reference SPR resonance angle signal generated in second half-through cavity 612. The resonant angle signal generated in first through window 606 is indicated by a dark bar 914 in band 906, and the resonant angle signal generated in second through window 608 is indicated by a dark bar 916 in band 908. The dark bar corresponds to the sharp dip of curve A or B in FIG. 2.

The resonance angles of dark bars 918 and 920 can be interpolated and/or extrapolated to determine the resonance angles of dark bars 914 and 916. The positions of dark bars are for illustration only. The actual positions and order of dark bars may be different from light pattern 900 shown in FIG. 9.

In another embodiment, the surface of prism 602 in first half-through cavity 610 is coated with the same thin metal layer (e.g., gold) as through windows 606 and 608. First half-through cavity 610 contains air only. The surface of prism 602 in second half-through cavity 612 is also coated with the same thin metal layer (e.g., gold) as through windows 606 and 608. However, second half-through cavity 612 contains a reference fluid dielectric medium, for example alcohol or other suitable materials. The detected dark bars will correspond to the SPR resonance angles generated in first half-through cavity 610 and second half-through cavity 612, which may be used for calibration of the incident angle of reflected light at the detector.

Of course, many combinations of critical angle, SPR resonant angle generated by the same metal layer and air, and SPR resonant angles generated by the same metal layer and reference fluid dielectric media, and SPR resonant angles generated by different metal layers and air, are possible.

While the present invention has been described herein with respect to the exemplary embodiments and the best mode for practicing the invention, it will be apparent to one of ordinary skill in the art that many modifications, improvements and sub-combinations of the various embodiments, adaptations and variations can be made to the invention without departing from the spirit and scope thereof. For the disclosed methods, the steps need not necessarily be performed sequentially.

The terms used in the following claims should not be construed to limit the invention to the specific embodiments disclosed in the specification and the claims. Rather, the scope is to be determined entirely by the following claims, which are to be construed in accordance with established doctrines of claim interpretation. The present specification and figures are accordingly to be regarded as illustrative rather than restrictive.

What is claimed is:

1. An apparatus for surface plasmon resonance measurement comprising:
   a prism;
   an incident light incident to a side of the prism and reflected at the side of the prism, the incident light comprising a first incident light having a first incident angle and a second incident light having a second incident angle; and
   a detector comprising pixels for detecting the incident light reflected at the side of the prism;
   wherein positions of pixels of the detector correspond to incident angles of the incident light; and
   wherein positions of pixels of the detector are calibrated by at least the first incident light having the first incident angle and the second incident light having the second incident angle.

2. The apparatus of claim 1, wherein the incident light covers a first area of the side of the prism, the incident light reflected at the first area of the side of the prism comprising the first incident light having the first incident angle having reduced intensity.

3. The apparatus of claim 2, wherein the incident light covers a second area of the side of the prism, the incident light reflected at the second area of the side of the prism comprising the second incident light having the second incident angle having reduced intensity, the second area is separated from the first area.

4. The apparatus of claim 3, wherein the first area of the side of the prism and the second area of the side of the prism are covered by half-through cavities of a tray facing the prism.

5. The apparatus of claim 4, wherein the first area of the side of the prism is not coated and the second area of the side of the prism is coated with a metal layer.

6. The apparatus of claim 4, wherein the first area of the side of the prism is coated with a first metal layer and the second area of the side of the prism is coated with a second metal layer, the first metal layer is different from the second metal layer.

7. The apparatus of claim 4, wherein the first area of the side of the prism is coated with a metal layer and the second area of the side of the prism is coated with the same metal layer, a first dielectric medium is disposed on the metal layer coated on the first area and a second dielectric medium is disposed on the metal layer coated on the second area, the first dielectric medium is different from the second dielectric medium.

8. The apparatus of claim 7, wherein one of the first dielectric medium and the second dielectric medium is air.

9. The apparatus of claim 4, the prism further comprising at least an area under a through window of the tray for providing a fluid dielectric medium.

10. The apparatus of claim 9, wherein the area under a through window of the tray is coated with a metal layer, and the fluid dielectric medium is disposed on the metal layer.

11. The apparatus of claim 1, wherein detecting the incident light reflected at the site of the prism comprising detecting reduction of intensity of the incident light.

12. The apparatus of claim 1, wherein the prism is a disposable and a new prism is installed for a measurement.

13. A method of auto-calibration for surface plasmon resonance measurement comprising:
   providing a prism comprising a first area and a second area of a side of the prism;
   providing an incident light incident to the side of the prism and reflected at the side of the prism, the incident light covering the first area and the second area of the side of the prism, the incident light comprising a first incident light having a first incident angle and a second incident light having a second incident angle;
   providing a detector comprising pixels;
   detecting the incident light reflected at the side of the prism wherein positions of pixels of the detector correspond to incident angles of the incident light; and
   calibrating positions of pixels of the detector by at least the first incident light having the first incident angle reflected at the first area of the side of the prism and the second incident light having the second incident angle reflected at the second area of the side of the prism.

14. The method of claim 13, wherein the first area of the side of the prism is not coated and the second area of the side of the prism is coated with a metal layer.

15. The method of claim 13, wherein the first area of the side of the prism is coated with a first metal layer and the second area of the side of the prism is coated with a second metal layer, the first metal layer is different from the second metal layer.

16. The apparatus of claim 13, wherein the first area of the side of the prism is coated with a metal layer and the second area of the side of the prism is coated with the same metal layer, a first dielectric medium is disposed on the metal layer coated on the first area and a second dielectric medium is disposed on the metal layer coated on the second area, the first dielectric medium is different from the second dielectric medium.

17. The method of claim 16, wherein one of the first dielectric medium and the second dielectric medium is air.

18. The method of claim 13, wherein the prism is a disposable and a new prism is installed for a measurement.

19. The method of claim 13 further comprising interpolating a first position of pixel corresponding to the first incident angle of the first incident light and a second position corresponding to the second incident angle of the second incident light.

20. The method of claim 13 further comprising extrapolating a first position of pixel corresponding to the first incident angle of the first incident light and a second position corresponding to the second incident angle of the second incident light.

* * * * *